United States Patent [19]

Comparetto

[11] Patent Number: 4,708,133
[45] Date of Patent: Nov. 24, 1987

[54] ARCUATE BONE CUTTER AND WEDGE GUIDE SYSTEM

[76] Inventor: John E. Comparetto, 322 Freeman Ave., Audubon, Iowa 50025

[21] Appl. No.: 721,640

[22] Filed: Apr. 10, 1985

[51] Int. Cl.$^4$ .............................................. A61F 5/04
[52] U.S. Cl. ............................... 128/92 VY; 128/92 R
[58] Field of Search ............... 128/92 H, 92 E, 92 R, 128/305, 305.1, 310, 92 XY, 92 ZW, 92 XV, 92 VY, 92 YE, 92 YF

[56] References Cited

U.S. PATENT DOCUMENTS

| 4,501,268 | 2/1985 | Comparetto | 128/92 H |
| 4,502,474 | 3/1985 | Comparetto | 128/92 E |
| 4,509,511 | 4/1985 | Neufeld | 128/92 H |
| 4,627,425 | 12/1986 | Reese | 128/92 VY |

FOREIGN PATENT DOCUMENTS 577020  10/1977  U.S.S.R. .............. 128/92 H

Primary Examiner—Albert J. Makay
Assistant Examiner—David W. Westphal
Attorney, Agent, or Firm—Shoemaker and Mattare, Ltd.

[57] ABSTRACT

A bone cutter comprising various curved blades and an adjustable radial arm for making arcuate cuts with the use of a reciprocating, saber or jig saw.

11 Claims, 16 Drawing Figures

ARCUATE BONE CUTTER AND WEDGE GUIDE SYSTEM

BACKGROUND OF INVENTION

Field of the Invention

The making of arcuate cuts in bone and the taking of precise wedges off these arcuate cuts.

Description of the Prior Art

Curved cuts in bone have been made excusively by the use of the crescentic or pivitol blade driven by the oscillating saw or by curved osteotomes. Each oscillating saw inherently has an arc from the center of this oscillating blade socket that it cuts most efficiently at. As the radius of oscillation increases or decreases from the optimal arc the efficiency of the saw blade decreases. Great difficulty has been experienced in the field in attempting to use any given manufacturers oscillating saw for multiple size arcs. Furthermore it has been necessary to buy a number of blades in assorted sizes which is an added expense. This is especially significant when one considers that only one arc size will effect truly efficient cutting.

OBJECTS OF THE INVENTION

An object of the invention is to provide a saw blade that will make efficient arcuate cuts in bone.

Another object of the invention is to allow the use of the reciprocating saw in making arcuate bone cuts.

Another object of the invention is to provide a housing within which a saw blade can travel while being powered by a reciprocating saw.

A further object of the invention is to provide a housing from which a pin can extend into bone.

A further object of the invention is to provide a hole within a housing within which the bone pin can articulate and allow the housing to pivot on the bone pin.

A still further object of the invention is to provide an adjustable arm in a saw blade housing that allows the saw blade to be adjustable in distance from the pivitol bone pin.

Another object of the invention is to provide a set screw to affix the adjustable arm of the housing.

A further object of the invention is to provide slot means within which fixation of the set screw can be made directly over the bone pin.

An essential feature of the invention is to provide a removable flute means that forms a slot for the guidance of straight cuts off the arcuate cut.

A further object of the invention is to provide a slot means that is angled from any radius of the arcuate cut.

A still further object of the invention is to provide a scalar means to measure excursions of the slot means along the arcuate cut.

Another object of the invention is to provide a scalar means that is offset from the blade housing and thus the immediate area of the surgical site.

An important feature of the invention is to provide a scalar means having a common center with each arcuate cut.

Another object of the invention is to provide a guide channel in the housing for the shank of a saw blade.

A still further object of the invention is to provide a saw blade having an arced and elongated body.

A further object of the invention is to provide a saw blade with saw teeth at right end of a curved elongated body.

Another object of the invention is to provide a saw blade having saw teeth at the left end of a curved and elongated body.

Another object of the invention is to provide saw teeth on both the right and left sides of a curved and elongated body.

A still further object of the invention is to provide a center of rotation offset from the center of rotation of the arcuate cut, the center of rotation to provide for the rotation of a compass means along the arcuate cut.

DETAILED DESCRIPTION OF THE INVENTION

Figure 1:
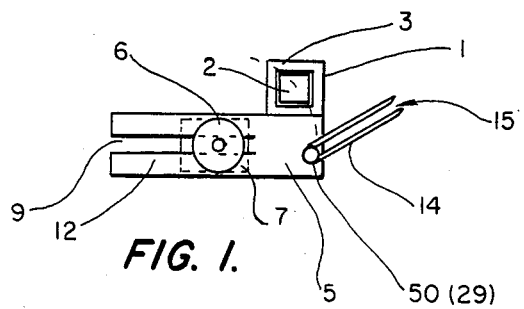
FIG. 1 is a view from above of an adjustable arcuate bone cutter.
Figure 2:
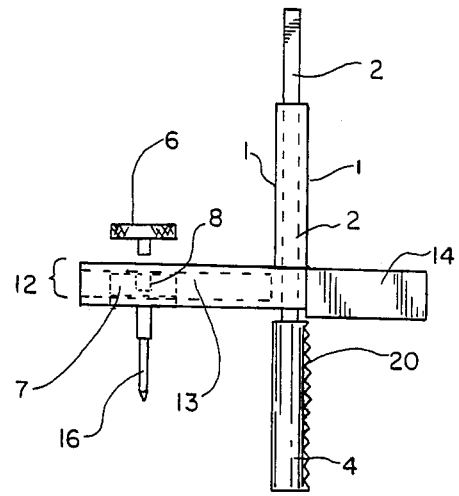
FIG. 2 is a side view of an adjustable arcuate bone cutter.

FIG. 1 depicts a bone cutter from above. Shaft (1) houses the blade shank (2) shown in cross section. Dashed curvature (3) indicates the path of the saw blade (4) seen in FIG. 2. Blade shaft (1) is connected to housing (5) and is an extension therefrom. Set screw (6) of FIGS. 1 and 2 affixes movable body (7) in screw hole (8). Slot opening (9) of FIG. 1 is formed by upper and lower slots (10) and (11) respectively in housing extension (12). Housing extension (12) is hollow and oblong (13) in these illustrations (FIG. 2), although the hollowness could be cylindrical or another uniform shape such as an elongate prism. Bone pin (16) is affixed to movable body (7) either permanently in which case after the bone pin is within the bone, the body (7) is slid into slot opening (9) to any desired depth and then affixed to flanges (19) formed by upper wall of the housing extension (12) and the upper slot (10). The set screw (6), screws into screw hole (8) of body (7) affixing the distance the bone pin is from the cutting saw blade, therefore affixing the center of the arc cut and the radial dimension of the arc from the bone pin. This radial dimension determines the size of the arc.

If the bone pin is permanently affixed to the movable body (7) then the pin would have to rotate in the bone to pivot the bone cutter. A perferred embodiment of the invention is to have the bone pin engage a hole within the movable body so that the cutter rotates on the end of the pin.

Unlike the arcuate (crescentic) saw blades (Weinstock) that have only one truly efficient blade arc per model of manufactured oscillating saw, the instant invention has maximum saw power employed at the chosen arc regardless of the arc size or the distance from the bone pin. A reciprocating saw (device not shown) is attached to the shank (2) of saw blade (4) after the bone cutting housing has been secured to the bone pin (16), the bone pin being selectively placed by the surgeon in a bone. The reciprocating saw device is then activated and the bone cutter is rotated on or with the bone pin, cutting an arc dictated by the distance of the cutting edge (20) from the bone pin. The reciprocating saw blade (4) moves up and down in the direction of the double arrows (22).

Figure 4A:
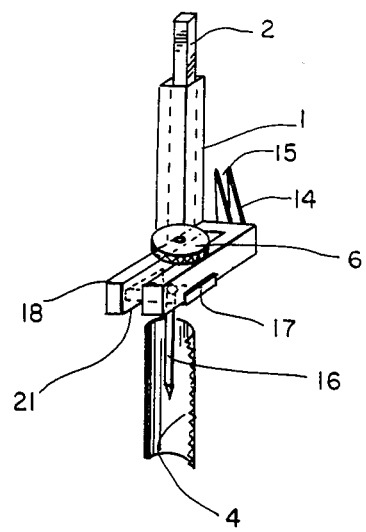
FIG. 4A is a perspective view of an arcuate bone cutter having a clamp to affix a bone pin.
Figure 4B:
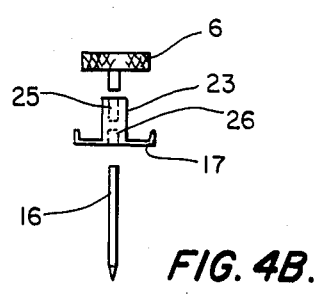
FIG. 4B is a planar view of the clamp of FIG. 4A.

Another embodiment of the invention is seen in the perspective view of FIG. 4A wherein solid housing extension (18) has a longitudinal slot (21) wherein body member (23) can freely move to any desired position. Body member (23) has two lateral flanges comprising a clamp (17) that engages the bottom of extension (18) while being affixed by set screw (6) which screws into body member (23) screw hole (25) (see FIG. 4B). The bone pin (16) engages body (23) in bone pin hole (26) on which the body can rotate.

Figure 12:
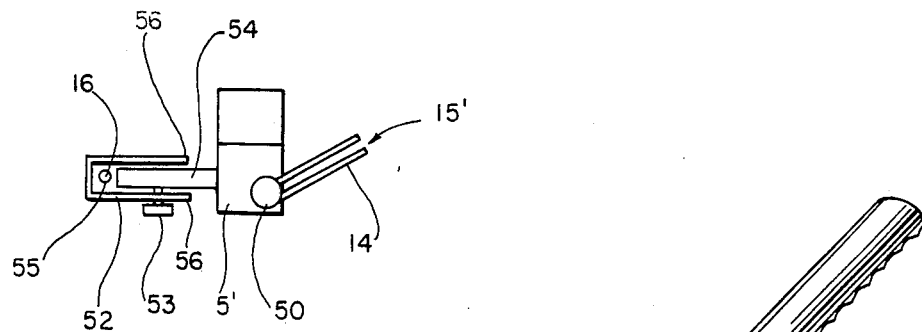
FIG. 12 is a view from above of another embodiment of the arcuate bone cutter.

In FIG. 12 we see another embodiment of the arcuate bone cutter that is comprised of an extension (54) which is rigidly attached to the housing (5). Movable hollow extension (52) can move along rigid extension (54) to any desirous extent whereupon it is affixed by a set screw (53) that can engage (54) from any face of hollow extension (52). Bone pin (16) will articulate with the hollow extension (54) through a suitable hole (55). The drawback to this embodiment is the limitation of the hollow extension as it will abut housing (5) at ends (56) and therefore will limit the adjustability at small radii.

Figure 5:
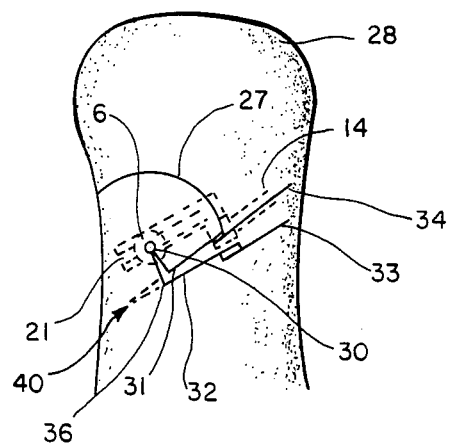
FIG. 5 is a view from above of a bone, the cuts, and the cutter.

At a point on the housing (5) parallel flutes (14) form a guidance slot (15). The flutes are angulated to form an acute angle with the saw blade pathway. This angulation of the flutes allows for the making of straight cuts through the slot member (15). The straight cuts will emanate from the curved bone cut; after the arced cut is made in bone straight cuts can be made to remove a wedge of bone. The arc cut (27), FIG. 5, is from one side of the bone ending within the bone at any desired point. This point is usually beyond the longitudinal bisection of the bone. With the saw blade within the bone at the innermost end of the arced cut the slot (15) is positioned over this same point. A partial straight cut is then made at least several millimeters into the bone from the end of the curved cut to the opposite side of the bone. The slot can now be repositioned at any other desired point on the arc that will be measured by various means and a second straight cut can now be taken from the arc to the other side of the bone. This second cut is made all the way through the bone. The first partial cut is now finished thus yielding a wedge which is removed. The bony parts are rotated along the section of cylinder made by the arcuate cut until the void made by the vacated bone wedge is closed. This new position is one of healing position while the bone has now been moved, one part relative to the other, an amount measured in degrees.

Figure 6:
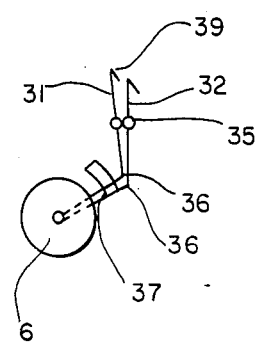
FIG. 6 depicts the compass legs.

In FIG. 5 set screw (6) is affixed on slot (21) which established bone pin set screw axis (30) which is of center of rotation of arcuate cut (27). Flutes (14) are positioned to form straight cuts (33) and (34). Legs (31) and (32) are angulated at elbow (36) of FIGS. 5 and 6 and can be used to measure the excursion of the flutes and guide slot and therefore the straight cuts. Each leg has a foot member (39) that can engage either the slot formed by the flutes or the first partial straight bone cut. A compass type measuring scale (37) can be used to measure the angular excursion of the legs and thus the size of the wedge. The legs can be adjustable with set screw (35) of FIG. 6, holding two separate segments of each legs (31) and (32) together at a desired length. If these lengths are equal and the dimension from one foot (39) to the other foot is measured, then the vertex (40) (FIG. 5) of the isoceles triangle formed can be computed from various geometric mensurations thus calculating the slot excursion.

Figure 7:
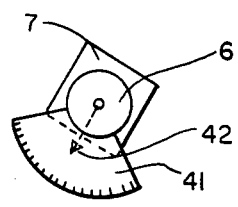
FIG. 7 is a view from above of a measurement scale.
Figure 8:
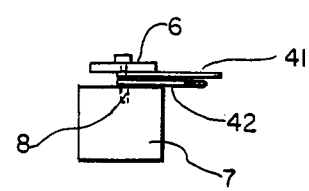
FIG. 8 is a view from the side of a scalar means.

In FIGS. 7 and 8, the scale (41) is held stable with set screw (6) while indicator arm (42) rotates in unison with the movable body (7) and therefore the housing and flutes. The indicator (42) is rigidly attached to the movable body (7).

Figure 9:
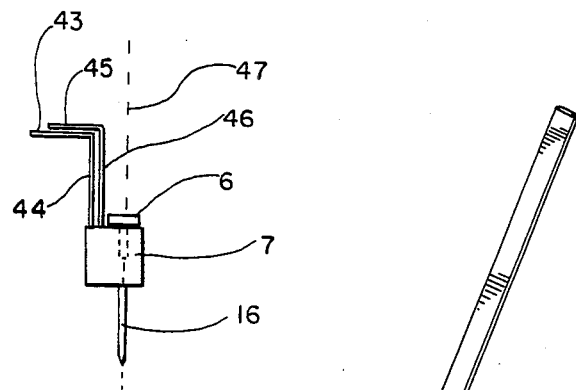
FIG. 9 is a view of a another scalar means with an offset center of rotation extended above the surgery site.

In FIG. 9 scale (43) rotates on body (7) on extension arm (44) while indicator (45) is rigidly affixed to body (7) by extension arm (46). The scale is held steady with indicator at 0°, the cutter and its flutes are then rotated. The movable body (7) and therefore the indicator (45) moves with the cutter describing the excursion in degrees on the scale which is still held stable. The rotation is accomplished on axis (47) which is the axis of the bone pin (16). The scale and indicator embodiment of FIG. 9 is relieved, by way of the extension arms, from the immediate surgical site.

Figure 10:
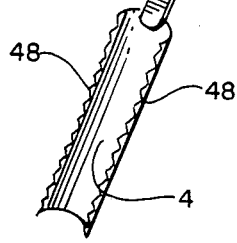
FIG. 10 is a perspective view of a double edged saw blade.

FIG. 10 depicts a saw blade having a curved body (4) and double blade edges (48) which can effect both left and right curved cuts in bone. A preferred embodiment of the invention would have saw teeth on only one edge right or left since while the leading edge is cutting bone from up and down movement of the reciprocal saw device, the trailing edge would also tend to cut bone thereby increasing the saw kerf which is undersirable.

Figure 3:
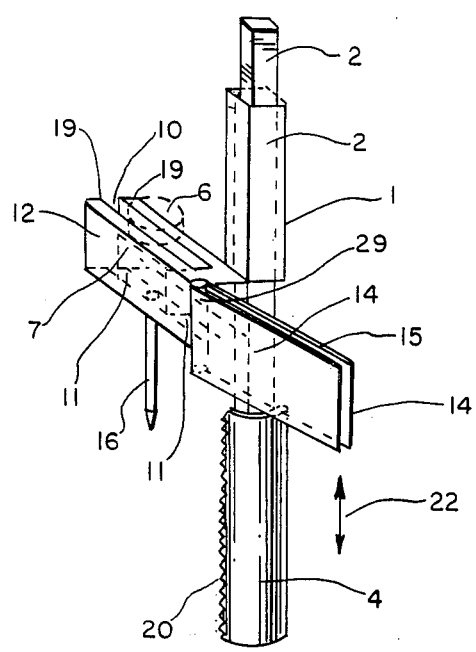
FIG. 3 is a perspective view of the arcuate bone cutter having a solid movable body in slot means.
Figure 11A:
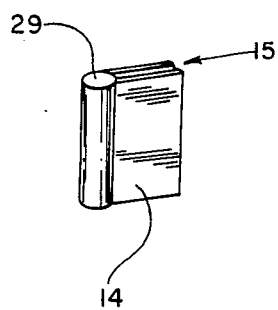
FIG. 11A depicts a removable flute system.
Figure 11B:
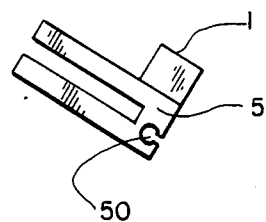
FIG. 11B depicts the channel into which the removable flute system is placed.

Within the housing shaft (1) a bushing of materials such as nylon can be used to reduce friction between the shaft (1) and the saw blade shank (2). These bushings would preferrably be disposable. Another disposable feature could be flutes (14) that are removable from the housing (5). An example of one means of a removable flute system would be flute post (29) of FIG. 3 that engages in a channel (50) within housing (5). FIG. 11A shows the flutes (14) attached to post (29) while FIG. 11B and FIG. 1 show the post channel (50) in housing (5).

The curvature of the body (4) of the saw blade adds strength to the blade by resisting flexure and buckling. This curvature although static in arc readily complies with various sized arc cuts, this is facilitated by the removal of the saw kerf which allows for the discrepancy. Preferably the curved section of the blade would be a precise arc of a circle to comply with a specific radius of the adjustable arm. For example, a 10 mm blade would refer to a blade most efficiently used when the adjustable arm is set at 10 mm; the arc of the blade having a radius of 10 mm.

Figure 13:
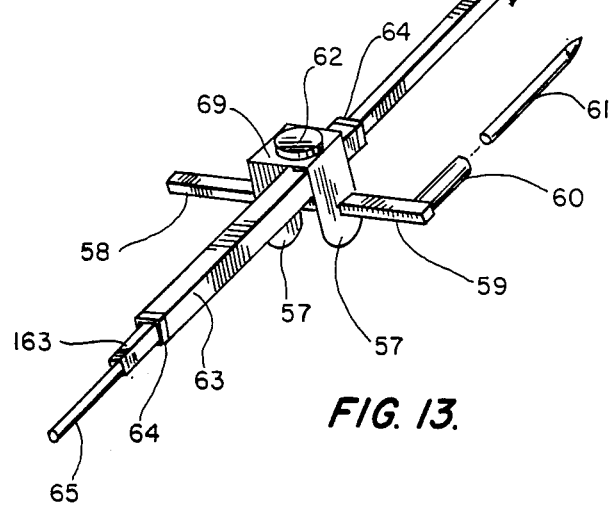
FIG. 13 is a perspective view of still another embodiment of the invention.
Figure 14:
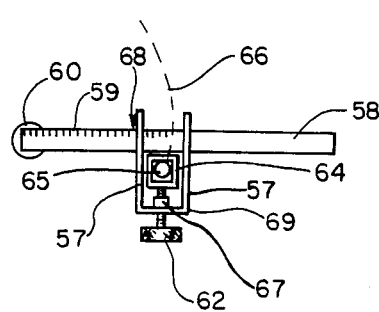
FIG. 14 is a view from above of the embodiment in FIG. 13.

A preferred form of the invention is seen in FIGS. 13 and 14 wherein bracket arms (57) hold adjustable arm (58) which can slide freely through the arms. Scale (59) measures the extent that bone pin holder (60) and therefore bone pin (61) is from saw blade path (66) and could be read at a convenient point such as (68) where the scale touches arm (57); the adjustment for the added distance to pathway (66) being built into the scale. Set screw (62) engages screw flange (67) in cross piece (69) of arm (57). The tip of the screw engages shaft (63) on one surface while causing arm (58) to bind against the opposite surface of the shaft (63). This pressure causes the arm (58) to affix at any desired excursion of the scale thus varying the radial arm of the bone cutter. This embodiment also allows the bone pin holder (60) to be adjusted vertically along the shaft. The shank (163) is attached to a reciprocating saw device through a suitable shank extension (65). The shank moves freely up and down within the shaft (63) coursing smoothly over the bushings (64) that can be removable.

From the foregoing description, one skilled in the art can easily ascertain the essential characteristics of this invention and without departing from the spirit and scope thereof, can make various changes and modifications of the invention to adopt to its various uses.

I claim:

1. A bone cutter comprising a saw blade having a shank and an elongate body extending therefrom, said elongate body being curved in cross section and having saw teeth along an elongate edge, said shank capable of attachment to a reciprocating saw device which makes up and down strokes, said shank smoothly articulating within a housing means comprising a shaft for said shank articulation, said housing means also comprising a hole means within which a bone pin is placed, said hole means being capable of adjustable movement with respect to said shaft and therefore said saw blade shank, such adjustable movement being arbitrarily affixed by a set screw, and flute means forming a slot extending from an area of the housing means that allows said slot to be positioned at its inner extent over the arc of the cutting blade body.

2. The bone cutter of claim 1 having saw teeth along two elongate edges of the curved saw body.

3. A bone cutter comprising a saw blade having a shank and an elongate body extending therefrom, said elongate body being curved in cross section and having saw teeth along an elongate edge, said shank capable of attachment to a reciprocating saw device which makes up and down strokes, said shank smoothly articulating within a housing means comprising a shaft for said shank articulation, said housing means also comprising a hole means within which a bone pin is placed, said hole means being capable of adjustable movement with respect to said shaft and therefore said saw blade shank, such adjustable movement being arbitrarily affixed by a set screw, and flutes forming a slot extending from the housing means at a point over the blade arc that is at an angle to the adjustable hole means of the housing.

4. A bone cutter comprising a saw blade having a shank and an elongate body extending therefrom, said elongate body being curved in cross section and having saw teeth along an elongate edge, said shank capable of attachment to a reciprocating saw device which makes up and down strokes, said shank smoothly articulating within a housing means comprising a shaft for said shank articulation, said housing means also comprising a hole means within which a bone pin is placed, said hole means being capable of adjustable movement with respect to said shaft and therefore said saw blade shank, such adjustable movement being arbitrarily affixed by a set screw, and an extension from said shaft, said extension capable of moving within an articulating housing section comprising a hollow arm means, and a set screw to affix said extension at any depth of insertion into said hollow arm means.

5. A bone cutter comprising a saw blade having a shank and an elongate body extending therefrom, said elongate body being curved in cross section and having saw teeth along an elongate edge, said shank capable of attachment to a reciprocating saw device which makes up and down strokes, said shank smoothly articulating within a housing means comprising a shaft for said shank articulation, said housing means also comprising a hole means within which a bone pin is placed, said hole means being capable of adjustable movement with respect to said shaft and therefore said saw blade shank, such adjustable movement being arbitrarily affixed by a set screw, and a slot means within an extension of said shaft means, said slot means allowing a set screw to pass through said slot means and affix in a screw hole of a clamp means, said clamp means being on the opposite side of said slot means and said clamp means being larger than said slot means, said clamp means having a hole within which a bone pin fits into said hole, said hole being on the opposite side of said clamp and in direct line with said screw hole, said set screw capable of engaging said clamp along any extent of said slot.

6. The clamp means of claim 5 wherein the bone pin is permanently affixed to said clamp means.

7. A bone cutter comprising a saw blade having a shank and an elongate body extending therefrom, said elongate body being curved in cross section and having saw teeth along an elongate edge, said shank capable of attachment to a reciprocating saw device which makes up and down strokes, said shank smoothly articulating within a housing means comprising a shaft for said shank articulation, said housing means also comprising a hole means within which a bone pin is placed, said hole means being capable of adjustable movement with respect to said shaft and therefore said saw blade shank, such adjustable movement being arbitrarily affixed by a set screw, and an extension from said shaft housing is hollow, a slot in an upper and lower wall of said hollow extension, a set screw, the screw portion of said set screw capable of passing into the upper slot and affixing to a screw hole in a solid body shaped to smoothly conformed to the interior of said hollow extension, said solid body capable of smooth travel along the inside of said hollow extension, said solid body further comprising a pin hole means on its directly opposite surface from said screw hole, said pin hole capable of engaging the end of a bone pin, said bone extending into said pin hole through said bottom slot of said hollow extension, said set screw capable of affixing said solid body at any point along said upper and lower slots.

8. The solid body means of claim 7 wherein the bone pin is permanently affixed to said solid body.

9. A bone cutter comprising a saw blade having a shank and an elongate body extending therefrom, said elongate body being curved in cross section and having saw teeth along an elongate edge, said shank capable of attachment to a reciprocating saw device which makes up and down strokes, said shank smoothly articulating within a housing means comprising a shaft for said shank articulation, said housing means also comprising a hole means within which a bone pin is placed, said hole means being capable of adjustable movement with respect to said shaft and therefore said saw blade shank, such adjustable movement being arbitrarily affixed by a set screw, and a scalar means having a center that is directly over the bone pin, said scalar means rotating on an adjustable set screw and further comprising an indicator movable upon said scalar means in conjunction with a housing means extension.

10. The scalar means of claim 9 wherein a scale indicates the degrees circular sector proscribed around the center set screw, said scale set above the set screw by an essentially vertical extension.

11. The process of drilling a bone to form a hole wherein a bone pin is placed, said bone pin entering a hole in a movable and adjustable segment of a bone cutter, said bone pin cooperating with said bone cutter to be the pivotal axis of an arcuate cut, said arcuate cut being made by an elongate saw blade moving up and down in parallel excursion with said bone pin axis, said elongate saw blade pivoting around said bone pin on an arched path from one side of the bone to a desired depth within the body of the bone thus forming a cut comprising a sector of a cylinder, a second saw blade that makes straight planar cuts being placed within a slot formed by flute means, said straight planar cuts extending from essentially the internal end of the arcuate cut in a manner angled to a radius of said arcuate cut outward to the other side of the bone, said planar cut being made only partially through the bone from top to bottom, a second planar cut being made within said slot means at a position desired away from the first partial straight cut along the arcuate cut, said second straight cut extending outward from the arcuate cut to the other side of the bone, said second straight cut further extending all the way through the bone from top to bottom, the process further comprising the completion of the straight partial cut all the way through the bone from top to bottom yielding a wedge of bone, said wedge of bone being removed, the resulting two bone sections being rotated one upon the other along the sector of cylinder formed by the arcuate cut until the void made by the wedge removal is closed in a healing apposition of the two bone sections.

* * * * *